United States Patent
Schuff et al.

(10) Patent No.: US 9,746,578 B2
(45) Date of Patent: Aug. 29, 2017

(54) APPARATUS FOR EXAMINING MOVING PRODUCTS, IN PARTICULAR MOVING PIECE GOODS, BY X-RAY

(71) Applicant: Wipotec Wiege- und Positioniersysteme GmbH, Kaiserslautern (DE)

(72) Inventors: Torben Schuff, St. Wendel (DE); Werner Thomas, Hochspeyer (DE)

(73) Assignee: Wipotec Wiege- und Positioniersysteme GmbH, Kaiserslautern (DE)

( * ) Notice: Subject to any disclaimer, the term of this patent is extended or adjusted under 35 U.S.C. 154(b) by 108 days.

(21) Appl. No.: 14/950,181

(22) Filed: Nov. 24, 2015

(65) Prior Publication Data

US 2016/0146968 A1   May 26, 2016

(30) Foreign Application Priority Data

Nov. 24, 2014   (DE) .......................... 10 2014 117 196

(51) Int. Cl.
*G01V 5/00* (2006.01)
*G01N 23/10* (2006.01)
(Continued)

(52) U.S. Cl.
CPC .......... *G01V 5/0016* (2013.01); *B65G 15/08* (2013.01); *B65G 15/28* (2013.01); *G01N 23/083* (2013.01);
(Continued)

(58) Field of Classification Search
CPC .. G01V 5/0016; G01V 5/0066; G01V 5/0008; G01V 5/0091; G01N 23/04;
(Continued)

(56) References Cited

U.S. PATENT DOCUMENTS 7,970,102 B2   6/2011   Gilevich et al.
2003/0031293 A1*   2/2003   Aust .................... G01V 5/0016
378/57

(Continued)

FOREIGN PATENT DOCUMENTS

DE   10309887 A1   11/2003
JP   2000241368 A   9/2000
(Continued)

*Primary Examiner* — Hoon Song
(74) *Attorney, Agent, or Firm* — The Webb Law Firm (57) ABSTRACT

Provided is an apparatus for x-ray examination of moving products, including a conveyor device with a conveying means on which a product to be irradiated rests in a movement plane. The product is transported in at least one of the following manners: along a predetermined movement trajectory at a predetermined speed; in accordance with a predetermined time-dependent course of speed or position; is rotated about a rotary axis that is substantially perpendicular to the movement plane, or any combination thereof. A radiation generating device, configured to generate an x-ray beam, is positioned on one side of the conveying means, and has a detector device, positioned on the opposite side of the conveying means. The radiation generating device is configured to generate an x-ray beam widening in fanlike fashion beginning at an x-radiation source of the radiation generating device.

20 Claims, 4 Drawing Sheets

(51) Int. Cl.
　　　*G01N 33/12*　　　(2006.01)
　　　*G01N 23/083*　　(2006.01)
　　　*B65G 15/08*　　　(2006.01)
　　　*B65G 15/28*　　　(2006.01)
(52) U.S. Cl.
　　　CPC ............. *G01N 23/10* (2013.01); *G01N 33/12* (2013.01); *G01V 5/00* (2013.01); *B65G 2207/00* (2013.01)
(58) Field of Classification Search
　　　CPC ....... G01N 2223/639; G01N 2223/643; G01N 23/10; G01N 2021/845; G01N 21/84; G01N 21/90; G01N 24/084; G01N 33/02
　　　See application file for complete search history.

(56) References Cited

U.S. PATENT DOCUMENTS

2004/0017882 A1　1/2004　Misawa et al.
2005/0105680 A1　5/2005　Nabors et al.
2006/0056584 A1*　3/2006　Allman ................ G01V 5/0008
　　　　　　　　　　　　　　　　　　　　　378/57
2009/0110143 A1　4/2009　Zhang et al.
2010/0020927 A1　1/2010　Gilevich et al.
2013/0251105 A1*　9/2013　Kotowski .............. G01N 23/04
　　　　　　　　　　　　　　　　　　　　　378/57
2015/0192690 A1*　7/2015　Bridger ................ G01V 5/0016
　　　　　　　　　　　　　　　　　　　　　378/57
2015/0294832 A1*　10/2015　Hakoda .................. B22D 46/00
　　　　　　　　　　　　　　　　　　　　　378/68

FOREIGN PATENT DOCUMENTS

JP　　2003260049 A　　9/2003
JP　　2008275451 A　　11/2008
JP　　2009109499 A　　5/2009
JP　　2009288200 A　　12/2009
JP　　　201268126 A　　4/2012

* cited by examiner

APPARATUS FOR EXAMINING MOVING PRODUCTS, IN PARTICULAR MOVING PIECE GOODS, BY X-RAY

CROSS-REFERENCE TO RELATED APPLICATION

This application claims priority to German Patent Application No. 10 2014 117 196.9 filed Nov. 24, 2014, the disclosure of which is hereby incorporated in its entirety by reference.

BACKGROUND OF THE INVENTION

Field of the Invention

The invention relates to an apparatus for examining moving products, especially moving piece goods, by x-ray.

Description of Related Art

For safety reasons piece goods, in particular containers filled with a medium, are checked in production lines mostly for the presence of foreign objects. Inspection systems suitable for this purpose often operate with x-rays, which penetrate the piece goods or rather the filled container and in doing so generate image data that enable the detection of foreign objects. It is understood that not only can foreign objects be detected in this manner, but characteristics of the piece goods or of the medium in the container in question, or of the container itself, can also be checked. For example, the presence and position of bones in pieces of meat or the percentage of fat in pieces of meat can be determined because different materials or substances absorb the x-rays penetrating the piece goods differently and thus damp the x-rays differently as well. It is also possible to assess the fullness of a filled container and check whether it is filled to a minimum fill level, for example.

Such x-ray inspection apparatuses typically operate with an x-ray beam that expands in a fanlike manner from an x-radiation source, which penetrates the piece goods to be inspected. The x-radiation source for this purpose is often mounted on the side of a conveyor device, for example a belt conveyor, so that the fanlike x-ray beam penetrates the piece goods from the side. On the other side of the conveyor device provision is made of a detector device, which detects the x-radiation not absorbed after it has penetrated the piece goods.

The fanlike x-ray beam usually has a beam plane that runs transversely, in particular perpendicularly to the conveying direction. The spread of the beam perpendicular to the beam plane is usually slight, but dependent upon the nature of the detector device. Many times use is made of detector devices in the form of a linear detector array, which has a plurality of pixels located equidistantly along a straight line. It is understood that the longitudinal axis of such a linear detector array must be aligned with the beam plane. In this case the spread of the x-ray beam perpendicular to the beam plane only needs to correspond approximately to the width of the pixels of the linear detector array. A wider beam (the spread of the beam perpendicular to the beam plane is referred to as the width) would not result in greater sensitivity because the energy contained in the width of the beam that is no longer detected by the pixels is lost. When use is made of a linear detector array, the resolution is generally defined by the area of the individual pixels and the spacing of the pixels. The pixel area and hence also the pixel width should therefore be selected within a range that ensures that the resolution generated thereby satisfies the requirements for detection precision.

As special linear detector arrays, use can also be made of so-called time delay integration (TDI) detectors, which have several detector lines running parallel to the beam plane but supply the (integrated) signal of the individual detector lines as an output signal. In this case the beam width should be wide enough that all rows of the TDI detector are covered by the beam width.

In all such line scanners, the moving product to be examined is scanned line by line (or slice by slice). The overall image of the product (or a section thereof) can then be generated, preferably as digital information, by assembling the individual lines (which correspond to x-rayed slices of the product).

More generally, however, use can also be made of an x-ray camera as a two-dimensionally operating detector in a detector device, wherein the x-ray camera is selected with respect to the detector area such that either the whole product or a section thereof is captured in one step. It is understood that several image sections can be reassembled into a whole image here as well. In this case the selected beam width must be at least as great as the width of the sensitive area of the camera, which can be configured as a two-dimensional digital sensor.

A prior art apparatus (InspireX R50S, Mettler-Toledo) for examining moving products employs an x-radiation source that is located on the side of a belt conveyor. The position of the x-radiation source is aligned with the surface of the upper run of the belt conveyor, on which the products to be examined lie. An x-ray beam of which the lower marginal beam runs essentially parallel to the belt surface (horizontally) can thus be generated and used. The bottom region of the product is thus penetrated by an essentially horizontal partial beam (beam bundle with a small opening angle (beam width)). This is advantageous if the floor area of a glass container, for example, is to be examined for damage. The lateral spacing of the position of the x-radiation source from the belt conveyor or rather from the product to be examined and the opening angle of the x-ray beam are selected such that the whole product will be penetrated by the fanlike beam.

In this apparatus, the position of the x-radiation source can be varied horizontally such that (if the opening angle of the beam remains constant) the beam can always be set such that the minimum possible beam height (measured, for example, at the position of the product with the minimum spacing from the x-radiation source in the beam plane) will always be used for a given height and shape of the product. In other words, the x-radiation source can be positioned such that all of the radiation energy always passes through the product (in the worst-case plane of the product, which requires the maximum beam angle for a given positioning of the product by the belt conveyor in the beam plane; in other positioning of the product, it is understood that a portion of the radiation energy can go past the product). For examining products of limited height, the x-radiation source can thus be moved close to the belt conveyor, or rather to the product, whereas for taller products, the spacing of the x-radiation source must be increased.

However, a disadvantage lies in this apparatus in that the upper edge zone of the product to be examined is always penetrated by partial beams running relatively obliquely (in the beam plane) upwards. This leads to a distortion of the respective image zone that is generated by the scanning. For certain application cases it is desirable if an upper zone or a zone at a predetermined height of the product to be examined is also penetrated by an essentially horizontally running partial beam when, for example, checking the top edge of a glass container for damage, checking the correct seating of a lid, or detecting the fill level (or rather the correct fill level) of a container.

To this end, it is possible to locate the x-radiation source at the same height as the top edge of the product and to define the beam angle such that the whole lower zone of the product is also penetrated by the x-ray beam. For adaptation to products of different heights, the position of the x-radiation source can then be adjusted accordingly in the vertical direction. Such a purely vertically moveable x-radiation source, however, requires a simultaneous adjustment of the beam angle, i.e., of the opening angle of the fanlike beam such that the lower product zone is also (just barely) x-rayed. Here it is essential to prevent a situation in which a major portion of the radiation energy does not pass through the product (in the worst-case plane) or an area of interest of the product fails to be x-rayed. The adjustment of the beam angle, however, requires additional effort.

As a solution, U.S. Pat. No. 7,970,102 B2 describes an apparatus for examining moving containers by x-ray, in which use is made of two x-radiation sources and two associated detector devices. A first x-radiation source is provided on the side next to the belt conveyor at the same height as the conveyor belt or rather the bottom side of the container to be examined, wherein the lower marginal beam of the x-ray beam runs essentially horizontally and the beam opens upwardly at a predetermined beam angle in the beam plane. The beam angle can be selected such that an upper portion of the container is no longer penetrated by this x-ray beam. A second x-radiation source is located laterally next to the belt conveyor at the same height as the container in question. The beam generated by this x-radiation source has an essentially horizontally running upper marginal beam. The beam opens downward at a predetermined beam angle. The beam angle of this beam can be selected such that a lower portion of the container is no longer penetrated. In this alternative, however, it is ensured that the whole product, i.e., all portions of the container, are examined with at least one of the two x-ray beams in use, with the main (middle) section of the container even being examined by both x-ray beams. The second, upper x-radiation source can also be configured as vertically adjustable for adaptation to containers of different heights. However, the adjustability is limited because it is necessary to ensure that every portion of the container is penetrated by at least one of the two x-ray beams.

Essentially two separate scanning devices are involved here, which can be located one after the other when viewed in the conveyor direction. However, they can also be located such that the containers are x-rayed in different (e.g., vertically superimposed) planes.

However, a disadvantage of this apparatus lies in the high expense for the two scanning devices.

SUMMARY OF THE INVENTION

On the basis of this prior art, the invention addresses the problem of creating an apparatus for examining moving products, in particular moving piece goods, by x-ray, which enables an essentially horizontal irradiation of the product to be examined in the area of the top edge or rather at a predefined height, in which the x-ray beam can be adjusted to products of different heights, and which is achievable as economically as possible. The apparatus should simultaneously enable x-raying and hence examining of a product, in the lower area thereof, with a partial beam running obliquely to the movement plane of the product.

The invention is based on the finding that a simple adaptation to products of different heights is possible by a linear displacement of the x-radiation source in a direction parallel to the direction of the lower marginal beam of the fanlike x-ray beam generated by the x-radiation source. It is thus ensured that the lower marginal beam always runs along the same trajectory and obliquely to the movement plane. The only thing that changes is the starting point of the lower marginal beam, which can be defined, for example, by the exit point of the fanlike x-ray beam on the x-radiation source. With a change of the position of the x-radiation source along the displacement trajectories, it is understood that the output density of the x-rays with which the product is irradiated changes. The movement plane is defined by the conveying means or rather by the contact area defined by the latter in which the bottom side or rather the bottom-most points of the product to be examined move.

The trajectory along which the displacement of the x-radiation source and thus of the fanlike x-ray beam takes place will normally be selected such that at least one desired lower area of the product to be examined is x-rayed. If the whole lower area of a product is to be x-rayed, in any case the lower marginal beam must also pass through the contact area or rather the bottom side of the product to be examined, with which the latter rests on the conveying means.

The fact that the direction and position of the lower marginal beam are essentially maintained during the displacement movement of the x-radiation source gives rise to the advantage that optimum use is made of the detector device or rather the sensor of the detector device, which is fixed in its position, even in the zone in which the lower x-rayed area of the product is imaged. It is understood that the height of the sensor of the detector device, which is located laterally on the conveying means, must be selected such that the upper marginal beam still impinges on the sensor, even in the highest positions of the x-radiation source.

At this point mention should be made that the invention does not require that the upper marginal beam run horizontally, but also includes embodiments in which the upper marginal beam runs in any direction. In such an embodiment, for example, the fill level of a container can be determined with great precision if the level, i.e., the top boundary surface, of the medium with which the container is filled has a greater spacing from the top edge area of the container. In this case the position of the x-radiation source is selected such that a parallel partial beam of the x-ray beam runs at the same height at which the expected fill level of the medium is located. In such an embodiment, the portion of the container above the fill level, for example the lid or lid area situated above the essentially horizontally running partial beam, can also be penetrated by that partial beam of the fanlike x-ray beam and thus inspected.

The movement of the product to be examined by irradiation can take place along a trajectory. It is understood that the trajectory can be a straight line, i.e., the products are moved linearly. Generally, however, the movement can of course take place along a trajectory of any configuration. In the area of the course of movement in which the product to be examined is x-rayed, however, the trajectory is preferably situated in a plane (for instance, a horizontal plane).

Such a movement of the product to be examined allows the product to be scanned with a fanlike x-ray beam, which has only a slight spread perpendicular to the beam plane, or by using a sensor which has only a slight spread in the movement direction, and which in particular can be configured as a line sensor.

However, the movement of the product to be examined may only be a rotation of the product about an axis perpendicular to the movement plane, in particular about a longitudinal axis or axis of symmetry of the product, i.e., in the zone of the fanlike x-ray beam, the product is rotated about an axis of rotation such that the x-ray beam irradiates the product along a different intersection plane in each case.

It is also possible to combine both of the aforementioned movements. The product can be conveyed along any trajectory in a zone in which the x-raying takes place. In this position a purely rotary motion of the product to be examined can be effected, for example by means of a rotating plate or a rotating disc whose contact area also defines the movement plane. After such a scanning of the product, the product can then be transported further along the predetermined trajectory.

However, it is also possible to execute the two movements simultaneously or quasi-simultaneously (in discrete steps, for example). The rotation of the product itself about an axis of rotation can take place simultaneously with the (further) conveying of the product.

In an embodiment of the invention, the x-radiation source can be configured and located such that the x-ray beam penetrates the conveying means over the entire width of the conveying means. In this case the conveying means must obviously be designed such that the lower marginal beam or rather the partial beam of the fanlike x-ray beam that passes through the conveying means still generates a usable image on the sensor of the detector device. The conveying means of the conveyor device must therefore be composed of a suitable material and/or be constructed in a suitable manner, at least in the area through which the partial beam in question passes. Because the x-radiation source is situated on one side of the conveying means of the conveyor device and the detector device or rather the sensor of the detector device is situated on the other side of the conveying means and thus of the product to be examined, the lower marginal beam always runs obliquely (i.e., not perpendicularly) to the surface of the conveying means on which the product lies. Accordingly, the conveyor device can have a portion that is not irradiated by the fanlike x-ray beam and which forms a stabilizing or bearing structure for the conveying means.

In another design of the invention, the x-radiation source can be configured and located such that the fanlike x-ray beam penetrates the conveying means in a width extending from the side facing the detector device to an edge area on the opposite side. In this embodiment then, a portion of the conveying means is not x-rayed. This portion of the conveying means can thus be composed of a material or have structural features that would hinder, or even render impossible, a correct imaging.

In a design of the invention, the conveyor device can be a belt conveyor and the conveying means can be an upper run of a power-driven endless belt. Such belt conveyors are widely available and represent an economical alternative of a conveying device. In principle, however, it is also possible to use any other type of conveying device for achieving the invention.

In an embodiment of the invention, the x-radiation source can be configured and located such that the lower marginal beam of the fanlike x-ray beam does not penetrate the return run of the endless belt. It is understood that the belt conveyor must be configured such that it has a thickness or rather depth that enables the lower marginal beam to leave the cross-sectional area of the belt conveyor before the lower marginal beam intersects the return run of the endless belt of the belt conveyor. In the cross-sectional area irradiated by the fanlike x-ray beam, the belt conveyor should of course be designed such that a correct imaging is possible.

In a design of the invention, the belt conveyor can comprise a belt body made of an x-ray reflecting and/or highly absorbent material, wherein a top run of the endless belt lies on a contact area of the belt body. In this embodiment, the belt body has a notch-like recess in the area of the x-ray beam, through which the x-ray beam passes. Hence the x-ray beam only passes through the upper run of the endless belt and the recess. The recess can be easily configured such that there is no or only slight interference, in particular damping and/or scattering of the x-ray beam.

For example, the conveyor device can be filled, at least in the zone of the contact area, with a material that essentially transmits the x-radiation completely or with only slight damping. In this manner the contact area can be closed again, even in the zone of the notch. The stability can be improved in this manner as well.

In another embodiment of the invention, at least a portion of the outer wall of the belt body in the zone of the notch-like recess that is not affected by the recess can function as part of a wall of a radiation protection housing. In particular this can be a part of an axial (in relation to the conveying direction of the trajectory in the product irradiation zone) peripheral wall of the radiation protection housing. The notch can thus be delimited by an x-ray absorbing and/or reflecting wall, for example on the bottom side of the belt body and/or on the side on which the x-radiation source is located. These can be either separate walls or outer walls of the belt body.

In a design of the invention, the belt body can be manufactured as an essentially U-shaped profile piece by bending an x-ray reflecting and/or highly absorbent, preferably planar plate-shaped piece, such as a piece of sheet metal, that has a perforation forming the recess for the x-ray beam. The belt body can be manufactured easily and economically in this manner. In particular, the recess of the belt body for the x-ray beam can be produced beforehand, by stamping or laser-cutting the plate-shaped piece.

The U-shaped profile piece can have two transverse walls made of an x-ray reflecting and/or highly absorbent material, preferably two sheet metal walls. Thus a first transverse wall, viewed in the conveying direction, can be provided before the recess and a second transverse wall after the recess for the x-ray beam. Additionally, a bottom wall together with the two transverse walls and zones of the top wall situated before and after the recess, respectively, can form a radiation trap, which absorbs at least a substantial portion of the energy of the x-radiation of the fanlike beam that does not penetrate the recess in an essentially straight path. In this manner it is possible to absorb scattered radiation in particular, which can arise as the x-radiation passes through the carrier run of the endless belt.

In an embodiment of the invention, the belt body can have in its contact area a channel that runs in a lateral edge zone of the contact surface. In particular this can be the edge zone of the contact surface that is no longer interrupted by the recess, wherein an engagement mechanism of the endless belt, preferably an elevation on the underside of the endless belt running in the conveying direction, engages in the channel in order to receive displacement forces acting transversely to the conveying direction on the carrier run of the endless belt, without the carrier run being displaced transversely to the conveying direction. Such a guiding of the endless belt often becomes necessary because a radiation protection room, which has openings in the direction of the incoming and outgoing product stream, is required with such apparatuses for examining moving products by x-ray. To prevent x-radiation from escaping from these openings, the products are shifted transversely to the conveying direction inside the radiation protection room in relation to the position in which they were introduced. Such shifting is usually effected, such that forces act on the endless belt transversely to the conveying direction, by slides or baffles. They can cause a displacement or distortion of the endless belt, which is prevented by the channel and the engagement mechanism.

The radiation generating device can have a linear displacement device, which is configured for the linear displacement of the x-radiation source together with a high voltage source of the radiation generating device. By displacing the actual x-radiation source jointly with the associated high voltage source, constantly having to move and in particular bend a suitable (i.e., suitably thick) cable between the moving x-radiation source and a stationary high voltage source is avoided. Stressing a suitably thick high voltage cable in this manner may damage it. To prevent this from happening, it would be necessary to use a suitably flexible and often expensive cable.

In a design of the invention, the radiation generating device can be configured together with the linear displacement device as a unit. The entire unit can then be designed such that it can be detached as a whole from the x-ray examination apparatus. This unit or rather the linear displacement device can also include the drive motor. However, the motor can also be configured separately from the unit composed of the radiation generating device and the linear displacement device and remain in the x-ray examination apparatus when the unit is uninstalled.

In an embodiment of the invention, the x-radiation source can be configured such that the upper marginal beam of the fanlike x-ray beam runs horizontally, wherein the evaluation and control unit is configured such that it controls the linear displacement device in such a way that the upper marginal beam essentially coincides with a predefined height position, in particular the height of each product to be examined.

However, the fanlike x-ray beam can also have a horizontally running partial beam, and the evaluation and analysis unit can be configured such that the linear displacement device is controlled in such a way that the partial beam essentially coincides with a predetermined height position, in particular the height of each product to be examined.

DESCRIPTION OF THE INVENTION

Figure 1:
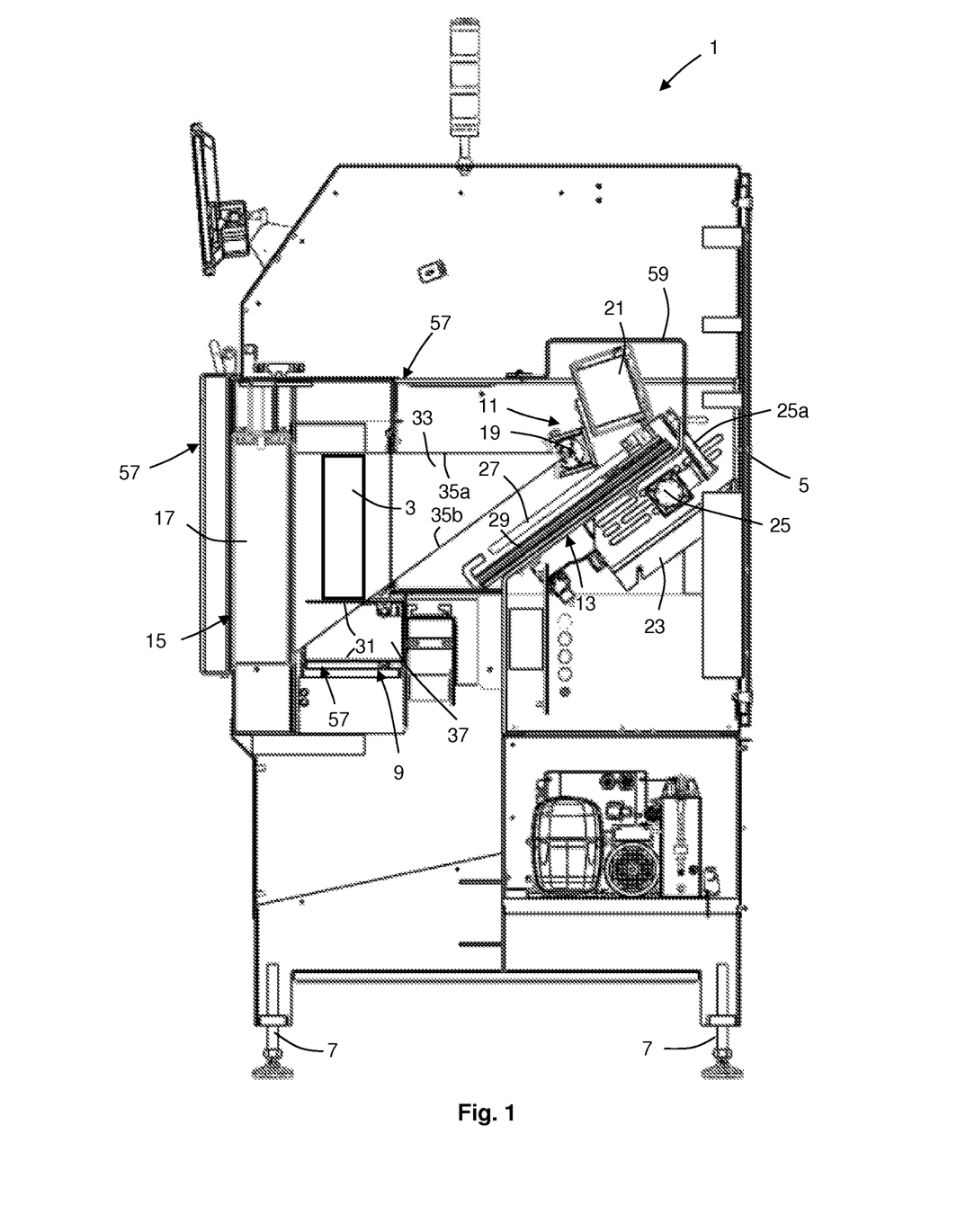
FIG. 1 is a section through an apparatus for examining moving products by x-ray according to the invention.

The apparatus 1 for examining moving products 3 by x-ray illustrated in FIG. 1 is configured as a floor-mounted apparatus and can be used in a production line (not illustrated). It is understood, however, it can also be directly integrated in a production line or production equipment. The apparatus 1 has a housing 5, which on its underside has apparatus feet 7 that are adjustable in height. The apparatus 1 further comprises a conveyor device 9, which in the illustrated exemplary embodiment is configured as a belt conveyor. In principle, however, any suitable conveyor device that enables the conveying of products 3 to be examined along a predetermined line (trajectory) can be used. The conveying preferably takes place at a constant speed. In principle, however, it is also possible to move the products 3 stepwise with a predetermined step size and, with the product 3 in question at a standstill in each case, to scan a preferably linear portion of the product 3. In principle, however, a non-uniform movement with (positive or negative) accelerations during the actual scanning, i.e., the data acquisition, is also possible.

The belt conveyor 9 transports the products 3 through the actual core element of the apparatus 1, which is formed by a linearly moveable x-radiation generating device 11, a linear displacement device 13, and a detector device 15 for capturing the x-radiation that is generated by the x-radiation generating device and impinges on a sensor 17 of the detector device 15. The resultant conveyor device for the movement of the products 3 is designated R (see FIG. 3).

As can be discerned in FIG. 1, the x-radiation generating device 11 comprises an x-radiation source 19, which draws the electrical power needed for generating x-rays from a high voltage source 21. The entire x-radiation generating device 11, i.e., the x-radiation source 19 and the high voltage source 21, is moved as a module by means of the linear displacement device 13 along a predetermined trajectory. It is thus possible to dispense with a large-diameter flexible special cable for supplying electrical power to the x-radiation source 19. Such a cable would have to be sufficiently flexible to enable the continuous linear movement of the x-radiation source. Such cables are quite expensive and also a potential source of trouble.

The linear displacement device 13 is mounted in a carrier frame 23, which is in turn mounted in an easily detachable manner in the housing 5. The entire unit consisting of the x-radiation generating device 11 and the linear displacement device 13 can thus be uninstalled as a whole from the housing 5 in modular fashion. This may be necessary for purposes of replacement, maintenance or repair.

It is understood that the linear displacement device 13 can have a drive of a known type, for instance a motor, in particular an electric motor, which drives a threaded spindle 27 either directly or via a transmission. The threaded spindle 27 can in turn drive a linearly guided carriage 29 on which the x-radiation generating device is located.

As shown in FIG. 1, the x-radiation generating device 11 together with the linear displacement device 13 is located such that the x-radiation source 19 is situated in a position laterally next to the product to be examined, or rather laterally next to the conveying means that moves the product to be examined. In the exemplary embodiment shown, an endless belt 31 of the belt conveyor 9 represents the conveying means. In general, however, the conveying means can be any suitable means of a conveyor device that (possibly after adaptation to the products to be conveyed) enables movement of the products. For example, it can also be an endless conveyor chain or a vibrating, slightly inclined plate on which the products move by gliding. The conveying means can also be a purely passive skid plate over which the product glides at a predetermined initial speed. Gliding on a cushion of air is also possible.

In the embodiment of FIG. 1, the x-radiation source is located laterally next to and above an imaginary horizontal lowermost movement plane, in which the underside or the lowest point of the moving product to be examined is located. This lowermost movement plane will hereinafter also be called the movement plane E. In many embodiments, it will extend horizontally, but this is not absolutely necessary.

The rectilinear line of movement along which the movement of the x-radiation source 19 or of the entire x-radiation generating device 11 occurs extends obliquely to the movement plane E, and for instance perpendicular to the conveying direction R. However, it is also possible to move the x-radiation source 19 or the x-radiation generating device 11 obliquely to the conveying direction R, as long as the motion has a component perpendicular to the conveying direction R.

As can be seen from FIG. 1, the x-radiation source 19 generates an x-ray beam 33, embodied in fanlike fashion, with an upper marginal beam 35a and a lower marginal beam 35b. The marginal beams represent the imaginary boundaries or edges of the x-ray beam 33, having a defined opening angle, and can each be considered to be a beam with an infinitely small opening angle. The fanlike x-ray beam 35 has a beam plane which is preferably, and in the exemplary embodiment shown, is vertical or perpendicular to the movement plane E of the products 3. In principle, however, it is also possible for the beam plane to be made to extend obliquely (but not parallel) to the movement plane and to embody and/or locate the x-radiation source 19 accordingly. Perpendicular to the beam plane, the x-ray beam 33 in the exemplary embodiment shown has only a relatively slight length, since a sensor 17 in the form of a line sensor is used. This sensor can have a single line, which is sensitive to the x-radiation and for instance—in the case of a digital sensor—has a plurality of pixels. However, a TDI line sensor can also be used, which has a plurality of lines the signals of which, adapted to the (constant) speed of motion of the products in the direction are pushed onward from one line to the next and thus integrated. However, in a TDI sensor as well, the image of a line, or of a corresponding "slice" of the irradiated product is furnished as an output signal. The term sensor or TDI sensor should include all components that directly convert the x-radiation, as well as components of the kind in which the x-radiation is first converted into a different spectral range, for instance via scintillators.

Of course the direction of the line sensor 17 must be selected such that it is aligned with the beam plane. The fanlike x-ray beam 33, after penetrating the product 3, must strike the sensitive region of the line sensor 17. If the x-ray beam 33, in the direction transverse to the beam plane, has a greater length than the sensitive area of the line sensor 17, then the line sensor 17 "cuts out" an image from the x-ray beam 33 that is equivalent to a "slice" of suitable thickness of the irradiated product 3.

In principle, it is also possible, instead of a line sensor, to use a two-dimensionally sensitive sensor 17 (area sensor). It can either make an image of a correspondingly larger portion of the product 3 as viewed in the conveying direction R, or even of the entire product. The prerequisite for this is understood to be a suitably adapted, broader x-ray beam.

The x-radiation source 19 and the linear displacement device 13 are embodied and located such that the lower marginal beam 35b extends without change in its position and direction, along the same line, even in the linear motion of the x-radiation source 19. Only the outset point of the lower marginal beam 35b changes. As a consequence, the lower marginal beam 35b always meets a lower region of the sensor 17 essentially at the same point or at the same height. This can preferably also be the lowermost sensitive point or the lowermost sensitive region of the sensor 17. As a result, it is attained that even upon a displacement of the x-radiation source, this lowermost irradiated region of the sensor 17 remains essentially unchanged. Upon a displacement, all that changes is the point that the upper marginal beam 35a strikes. The imaging of the product 3 to be examined is thus always effected such that the lower or lowermost irradiated region of the product 3 is detected by an associated lower or lowermost region of the sensor 17.

Typically, the lower marginal beam 35b will be chosen with regard to the position of the product 3 to be examined and the embodiment of the conveyor device 9 in such a way that the entire product, or the entire lower region of the product 3, is irradiated. However, it is of course also possible to define the lower marginal beam 35b such that a predetermined lower portion of the product 3 is not irradiated, for instance if that region is not critical or is of no interest with respect to the inspection of the product that is to be done.

If desired, the lower marginal beam can also extend obliquely upward; for that purpose, it is understood that the x-radiation source 19 or the entire x-radiation generating device 11 and the linear displacement device 9 be positioned laterally below the movement plane of the products 3. The upper marginal beam 35a in that case extends more steeply (upward) than the lower marginal beam 35b. In this case as well, the sensor is always used completely in its lower region, regardless of the height of the products to be examined and regardless of the position of the x-radiation source 19.

In this embodiment as well, the advantage is attained that for detecting certain error sources, the bottom region of the product to be examined is irradiated obliquely. For instance, glass splinters that are located in the bottom region of the container volume, even with curved bottoms that have a central indentation, for instance, can be reliably detected. This is because the partial beams extending obliquely pass through the container walls (including the bottom of the container) a maximum of two times, while a horizontally extending partial beam would pass through container walls many times and as a result, foreign bodies of the same kind would be difficult to detect or would not even be detectable at all anymore.

In the embodiment of an apparatus 1 shown in FIG. 1, the x-radiation generating device 11 or the x-radiation source 19 of the apparatus 1 for x-ray examination of moving products is embodied and located in such a way that the upper marginal beam extends horizontally or parallel to the movement plane. This has the advantage that certain properties of a product can be detected with good precision, or even for the first time with the desired certainty, at the height of the horizontally extending upper marginal beam 35a. For instance, the fill level of a vessel filled with a medium can be detected with greater precision if the level extends approximately parallel to the course of the applicable partial beam or of the upper marginal beam 35a. Examining the upper edge of a product or vessel, such as the upper edge of a glass vessel, can also advantageously be inspected in this way, for instance to check for the presence of damage.

In this way, it is possible in particular to monitor the intactness of the thread of a glass bottle or glass container, especially when it has already been closed with a screwed-on cap. This is because in such containers, the glass thread may already have been damaged by screwing on the cap, so that when the cap is opened by the user, chips from the glass thread drop into the container and then certainly contaminate the food. Glass tolerances can cause glass splinters to chip off from the thread in such containers. Especially when the cap is put or screwed on automatically, then in unfavorable circumstances splinters of glass can be chipped off in the region of the thread. In such containers, it is possible to find such defects after caps have been screwed on because of the preventive precise survey of the cap region that is done by x-ray examination. The defective products or containers can then be discarded before being put into commerce.

In principle, the upper marginal beam 35*a* need not be used for examining a specific region of a product using a horizontally extending partial beam. In the case of an x-ray beam 33 embodied in fanlike fashion, which includes a horizontal partial beam as well, this can also be done in such a way that the apparatus 1, as a function of the position of the x-radiation source 19, knows the position or height at which the applicable horizontal partial beam strikes the sensor 17 of the detector device 15.

Figures 2, 3:
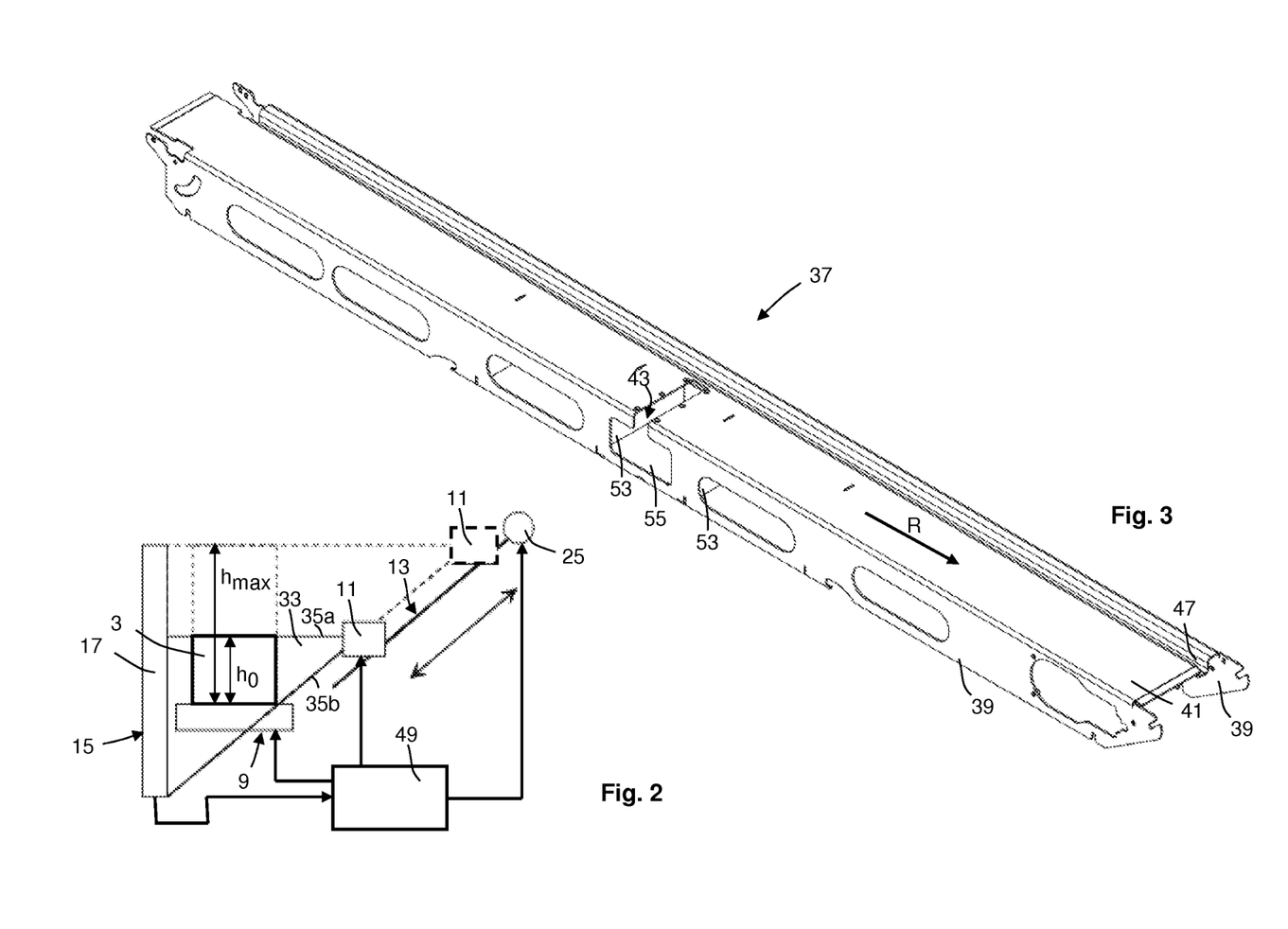
FIG. 2 is a schematic view of the preferred components of the apparatus in FIG. 1 illustrating the linear movement of the x-radiation source.
FIG. 3 is a perspective view of a belt body of the conveyor device used for the apparatus in FIG. 1.

In the apparatus 1 shown in FIG. 1, the belt conveyor 9 shown in section is shown only in simplified form. The endless belt 31 travels about a belt body 37 and is driven by a motor, not shown in detail. The belt body 37 is shown in FIG. 3 in a perspective view. The belt body 37 has a profile that is essentially U-shaped in cross section, which has two side walls 39 and one top wall 41. The endless belt 31 is driven by a motor, not shown in detail, in particular an electric motor. The endless belt 31 is further guided about two deflection rollers, also not shown in detail, which are each located on the end of the belt body 37 and are rotatably supported. One of the two endless rollers can be driven by the electric motor. A chucking mechanism may be provided, which for instance subjects one of the deflection rollers to a spring force, so that in particular the upper run of the endless belt 31 is subjected to a predetermined chucking power. The upper run of the endless belt 31 rests on the top of the top wall 41.

In the region in which the fanlike x-ray beam 33 intersects the conveyor device 9 and thus also the cross section of the belt body 37, the belt body 37 has a notchlike recess 43. The width of the recess (viewed in the longitudinal direction of the belt body 37) is at least great enough that the portion of the radiation energy of the fanlike x-ray beam 33 that also strikes the sensor 17 of the detector device 15 can pass unhindered through the belt body. This prevents the x-ray beam 33, on passing (in particular, unevenly) through the cross section of the belt body 37, from being absorbed (that is, damped) by the material of the belt body 37 and/or reflected. Such a recess 43 in the belt body 37 is especially necessary whenever, as is often the case, the belt body comprises a material, such as a metal, that is impenetrable to x-radiation and/or absorbs and/or reflects it to a high degree.

In a belt body 37 having the construction shown in FIG. 3, the notchlike recess 43 is provided in particular in a part of the side wall 39 and of the top wall 41. The notch in the top wall 41 of the belt body 37 can also be closed with a material that does not damp, or only weakly damps, the x-radiation and/or weakly reflects it, such as a plastic (for instance, PEEK). The entire recess 43 may also be filled with a material that does not or only weakly damps the x-radiation and/or weakly reflects it.

As can be seen from FIG. 3, viewed in the conveying direction R, a transverse wall 53 extending vertically can be provided both upstream and downstream of the recess 43; together with a bottom wall 55, each transverse wall forms a radiation trap for that portion of the x-radiation that does not pass through the recess 42 in a straight path. For instance, x-radiation whose direction is varied by the irradiated material or the irradiated product 3 and/or by the material of the irradiated conveyor means or endless belt 9 (in particular scattered radiation or reflected radiation) and which enters the radiation trap can be absorbed so much by multiple reflection inside the radiation trap that when this radiation escapes, its intensity is no longer dangerous to humans or machines. The transverse wall 53 and the bottom wall 55 can comprise a material that reflects and/or at least partially absorbs x-radiation. Instead or in addition, the insides of these walls can also be provided with a corresponding layer of a suitable material. On its top side, the radiation trap is bounded by those (horizontally extending) regions of the top wall 41 in which the recess 43 or its portion does not extend in the top wall 41.

The bottom wall 55 of this radiation trap can also, as can be seen from FIG. 1, form a part of a radiation protection wall or a radiation protection housing 57. The radiation protection housing 57 is almost completely closed on all sides and has only an inlet opening and an outlet opening for delivering the products 3 into and uninstalling them from the radiation protection housing 57. As viewed in the conveying direction R, the radiation protection housing can essentially be limited to the width of the x-ray beam 33 in this dimension. For safety reasons, however, the radiation protection housing will be provided with a greater width in this direction as well.

As seen in FIG. 1, the radiation protection housing 57 can have a removable lid or a removable housing part 59, which serves in the event of maintenance or repair to uninstall the x-radiation generating device 11 from the radiation protection housing 57. To that end, advantageously, the x-radiation generating device 11 together with the x-radiation source 19 and the high-voltage source 21 can be embodied as a unit with the linear displacement device 13. This entire unit can then be uninstalled as a whole from the radiation protection housing 57 by undoing a suitable fastening, for instance by undoing one or more screws. The fastening can also be embodied as a quick-action chucking device which can be actuated without tools. This makes maintenance, repair or replacement considerably easier.

In the variant shown in FIG. 1, the motor 25 and the carrier frame 23 are located outside the radiation protection housing 57, and they remain in the apparatus 1 when the module that includes the x-radiation generating device 11 with the x-radiation source 19 and the high-voltage source 21 and also includes the carriage 29 is uninstalled. For uninstalling the module, the drive merely has to be uncoupled from the carriage 29. To that end, a drive belt 25*a*, such as a toothed belt, that is passed through the radiation protection housing 57 is disconnected from the applicable drive element of the carriage 29, namely from the spindle 27.

Figure 4:
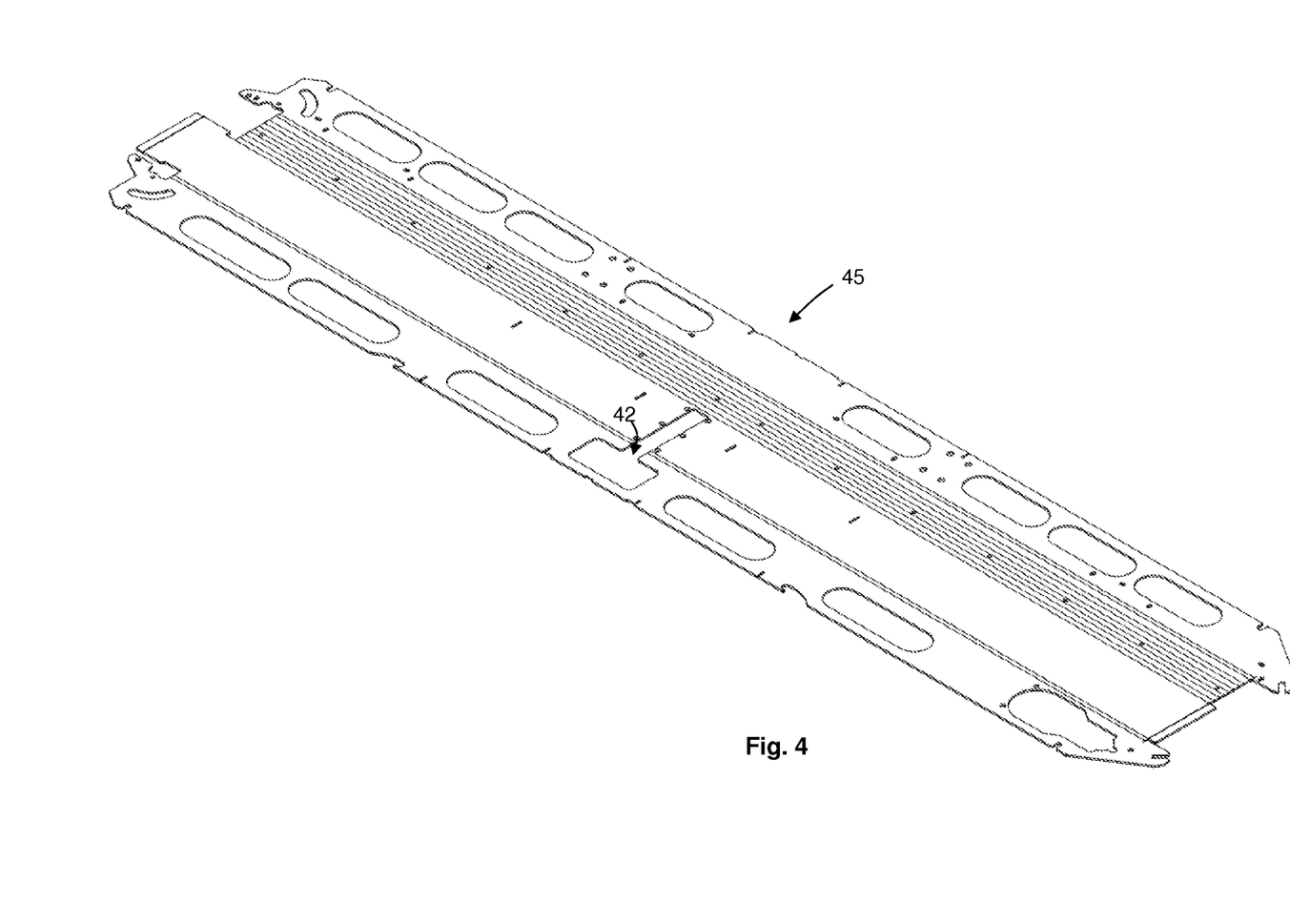
FIG. 4 is a perspective view of a piece of sheet metal for manufacturing the belt body in FIG. 3.

As can be seen in FIG. 4, the belt body 37 shown in FIG. 3 is preferably made from a flat, plate-shaped, prefabricated element 45, such as a metal sheet. The element 45 is preferably produced in the flat state with the requisite recesses or apertures. In particular, these can be apertures for receiving shafts or bearings for the deflection rollers (not shown), and an aperture 42 that after bending forms the recess 43 for the x-ray beam 33.

It can also be seen from FIG. 3 that in the peripheral region of the top, or in other words of the top wall 41 of the belt body 37, that the x-ray beam 33 does not pass through, a channel 47 extending in the direction of motion of the endless belt 31 is provided. In FIG. 3, to simplify the drawing, only the bending edges of the channel 47 are shown. These bending edges are also shown in FIG. 4.

In closing, the function of the apparatus 1 for x-ray examination of moving products 3 will be explained in terms of the schematic view in FIG. 2. FIG. 2, in a first position represented by solid lines, shows the x-radiation generating device 11 in a lowermost position. In this position, in particular products 3 with a minimum height $h_0$ can be examined. The upper marginal beam 35a extends essentially (horizontally) in alignment with an uppermost movement plane (parallel to the movement plane E) of the product 3 (in which uppermost plane, the highest point of the product 3 is moved). Thus the uppermost region of the product 3 having the height $h_0$ can be examined with a horizontally extending partial beam (namely, the uppermost marginal beam 35a).

In a second, uppermost position, the x-radiation generating device 11 is shown with dashed lines. In this uppermost position, products 3 with a maximum height $h_{max}$ can be examined; in this position as well, the upper marginal beam 35a extends in horizontal alignment with the uppermost movement plane. The motion of the x-radiation generating device 11 is effected, between the uppermost and the lowermost position, in a direction of motion parallel to the direction of the lower marginal beam 35b.

As already explained above, the lower marginal beam 35b, in every possible position between the two extreme positions shown in FIG. 2, meets the sensor 17 of the detector device 15 at the same point or the same position. Only the height at which the upper marginal beam 35a strikes the sensor 17 varies.

It is not absolutely necessary that the height of the upper marginal beam 35a be aligned with or flush with (or protrude slightly beyond) the height of the particular product 3 to be examined. The position of the x-radiation generating device 11 can also be adjusted such that the upper marginal beam is aligned with a predefined height, at which the product 3 is to be examined with the horizontally extending upper marginal beam 35a. This height can be the fill level of the applicable product (container).

Controlling the position of the x-radiation generating device 11 and/or of the x-radiation source 19 and triggering the conveyor device or the belt conveyor 9 can be done by an evaluation and control unit 49. For adjusting the position of the x-radiation generating device 11, the evaluation and control unit 49 triggers the motor 25 of the linear displacement device 13. The evaluation and control unit 49 itself can activate and deactivate the x-ray beam 33 and vary its power by triggering the x-radiation generating device 11. The evaluation and control unit 49 can also be embodied such that it triggers the conveyor device or the belt conveyor 9 with regard to its speed. This can also involve triggering in the sense of a movement profile. The drive or the motor 25 can also have an encoder for this purpose, in order to enable an exact triggering of positions within the movement profile. From the detector device 15, the evaluation and control unit 49 receives a signal that contains the image information detected by the sensor 17.

In this way, it is possible for the evaluation and control unit 49 to adapt the position of the x-radiation generating device 11 to the height of the products 3 to be examined. This can either be done in that the evaluation and control unit 49 is supplied with appropriate information from a higher-order control unit (not shown).

However, the evaluation and control unit 49 may also be embodied such that it makes an automatic adaptation of the position of the x-radiation source 19 to either the height of the product 3 to be detected or the fill level height to be detected. For that purpose, the evaluation and control unit 49 can first detect or examine the product to be detected in the uppermost position of the x-radiation generating device 11 and then, from the image generated in this way, ascertain the height of the applicable product 3. The detected product 3 can be moved back again by suitable triggering of the conveyor device 9 and, after the x-radiation generating device 11 is put into the desired position, the product can be moved forward again and examined. The x-radiation generating device 11 can then be left in the position thus ascertained until such time as the evaluation and control unit 49, from the currently detected image of a product 3, finds that the upper end of the product 3 is no longer being included in the image. This finding can then be made, if the position of the x-radiation generating device 11 is always chosen such that the x-ray beam 33, with its upper marginal beam 35a, makes complete detection of the product at its full height possible. To do so, the position of the x-radiation generating device 11 must be selected such that the upper marginal beam 35a is located slightly higher than the maximum height of the product 3 in question that is to be examined.

Thus the invention ensures the simple adaptation of the fanlike x-ray beam, generated by means of the x-radiation source 19, to the height of a product 3 that is to be examined. By displacement of the x-radiation generating device 11 or the x-radiation source 19 in a direction parallel to the lower marginal beam 35b of the fanlike x-ray beam 33, the advantage is attained that the lower marginal beam always strikes the sensor 17 at the same position, regardless of the product height. The position of the lower marginal beam 35a can be selected such that a complete image of precisely the entire lower region of the product 3 to be examined still reaches the sensor 17. It is understood that it is also possible to define the lower marginal beam 35a in such a way that a particular lower region of the product 3 that is not of interest is not detected.

An upper, horizontally extending marginal beam 35a or a horizontally extending partial beam (located in the vicinity of the fanlike x-ray beams 33) can be selected, by means of a simple positioning of the x-radiation generating device 11, such that this x-radiation generating device is located at a desired height of the product, in particular at the height of a fill level, or in the vicinity of the upper product edge where a container lid can be located.

If the x-radiation generating device 11 is positioned such that the x-ray beam generated passes through no more than the height to be examined of the product 3, then the x-ray power required for the examination can be minimized. The evaluation and control unit 49 can trigger the x-radiation source 19 in such a way that the irradiation intensity of the x-radiation remains constant. In examining products 3 of lesser height, the power of the generated x-radiation transported by the fanlike x-ray beam 33 can thus be less than when irradiating products 3 of greater height, or when irradiating a larger region of a product 3. By reducing the x-radiation power, the service life of the x-radiation sources can be lengthened.

Figure 5:
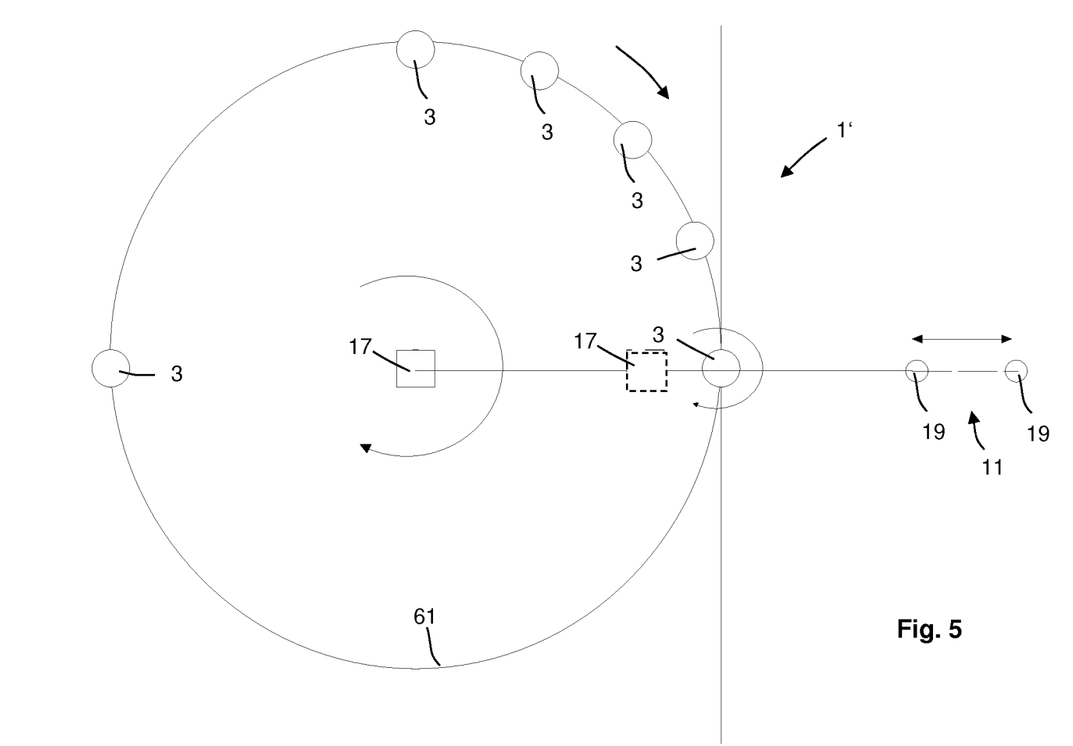
FIG. 5 is a schematic view from above of another embodiment of an apparatus for the x-ray examination of products moving on a circular path.

In FIG. 5, a further embodiment of an apparatus 1' for x-ray examination of moving products 3 is shown in a schematic plan view. The products 3 are moved along a movement trajectory 61. In the exemplary embodiment shown, the movement trajectory 61 is embodied as a circular path. The sensor 17 is positioned at the center of the movement trajectory 61. The detection direction of the sensor 17 points radially outward. In FIG. 5, a product 3 to be examined is shown in a detection position. The x-radiation generating device 11, which of course again has an x-radiation source 19 and a high-voltage source 21 that as described with reference to FIGS. 1 through 4 is embodied displaceably by means of a linear displacement device not shown in detail in FIG. 5, is provided at a position located opposite the sensor 17 with respect to the movement trajectory 61. The fundamental functionalities of the sensor 17 and the x-radiation generating device 11 can be embodied identically, as has been explained above in connection with FIGS. 1 through 4.

As indicated by dashed lines in FIG. 5, however, the sensor 17, or the entire detector device 15, can also be provided not at the center of the circular movement trajectory 61, but at a position closer to the detection position.

With a thus-embodied apparatus, the examination of the product can be done in the same way as has been explained above in conjunction with FIGS. 1 through 4, namely by means of a continuous or incremental movement along the belt body, which in this embodiment no longer extends purely linearly in the detection region. It is understood that the product 3 can be scanned either line by line or in increments, or, if a suitable area sensor is used, by means of a single irradiation or imaging operation.

As indicated in FIG. 3, the product 3 in its detection position or in the detection region can be rotated by the conveying means not shown in detail in FIG. 3, after reaching its detection position, only about one axis, preferably a longitudinal or vertical axis, of the product 3. To that end, the conveying means can be embodied in the detection region as a turntable or rotary disk; the top side of the rotary disk forms the movement plane E. The rotary motion of the product 3 is then effected continuously or incrementally in such a way that the product to be examined is irradiated or examined in a different plane each time.

It is understood that it is also possible to combine the aforementioned two motions; that is, the product 3 to be examined is both transported along the predetermined movement trajectory 61 and rotated about a rotary axis. The precondition is understood to be a somewhat more complex conveying means.

In this case as well, the conveying means must be embodied such that the lower marginal beam 35b extending obliquely to the movement plane E, or that part of the fanlike x-ray beam 35 can pass through the movement means at least with sufficiently slight damping and scattering so as to ensure reliable examination of the product 3 in its lower region as well.

It is understood that it would also be possible to dispense with moving the product 3 along a predetermined movement trajectory and manually, or by means of a robot or some suitable device, to put the product 3 in the detection region in which a rotational motion of the product 3 is then performed.

In all these variants, because of the embodiment of the x-radiation generating device 11 in such a way that the movement of the x-radiation source 19 is effected parallel to the direction of the lower marginal beam 35b of the fanlike x-ray beam 35, the advantages described above with respect to the embodiment of FIGS. 1 through 4 are obtained.

1, 1' Apparatus for x-ray examination of moving products
3 Product
5 Housing
7 Foot of the apparatus
9 Conveyor device/belt conveyor
11 X-radiation generating device
13 Linear displacement device
15 Detector device
17 Sensor
19 X-radiation source
21 High-voltage source
23 Carrier frame
25 Motor
25a Drive belt
27 Threaded spindle
29 Carriage
31 Conveyor means/endless belt
33 Fanlike x-ray beam
35a Upper marginal beam
35b Lower marginal beam
37 Belt body
39 Side wall
41 Top wall
42 Aperture
43 Recess
45 Plate-shaped element
47 Channel
49 Evaluation and control unit
53 Transverse walls
55 Bottom wall
57 Radiation protection housing
59 Lid
61 Movement trajectory
$h_0$ Minimum height
$h_{max}$ Maximum height
R Conveying direction
E Movement plane

The invention claimed is:

1. An apparatus for x-ray examination of moving products, comprising:
   (a) a conveyor device with a conveying means on which a product to be irradiated rests in a movement plane, wherein the product is transported in at least one of the following manners: along a predetermined movement trajectory at a predetermined speed; in accordance with a predetermined time-dependent course of speed or position; rotated about a rotary axis that is substantially perpendicular to the movement plane, or any combination thereof; and
   (b) a radiation generating device, configured to generate an x-ray beam, positioned on one side of the conveying means, and having a detector device, positioned on the opposite side of the conveying means,
   (c) wherein the radiation generating device is configured to generate an x-ray beam widening in fanlike fashion beginning at an x-radiation source of the radiation generating device, wherein the x-ray beam has an upper and a lower marginal beam and passes through the product,
   (d) wherein the detector device detects the x-ray beam striking it and converts it into a signal, which is supplied to an evaluation and control unit,
   (e) wherein the lower marginal beam of the x-ray beam extends obliquely to the movement plane, and
   (f) wherein the x-radiation source is positioned in linearly displaceable fashion in a direction parallel to the direction of the lower marginal beam of the fanlike x-ray beam.

2. The apparatus of claim 1, wherein the x-radiation source is configured and positioned such that the x-ray beam penetrates the conveying means in the entire width of the conveying means.

3. The apparatus of claim 1, wherein the x-radiation source is configured and positioned such that the x-ray beam penetrates the conveying means in a partial width, beginning at the side toward the detector device, to a marginal region that is not irradiated on the opposite side of the conveying means.

4. The apparatus of claim 1, wherein the conveyor device is a belt conveyor and the conveying means is an upper run of a driven endless belt.

5. The apparatus of claim 4, wherein the x-radiation source is configured and positioned such that the lower marginal beam of the x-ray beam does not penetrate a lower run of the endless belt.

6. The apparatus of claim 4, wherein the belt conveyor includes a belt body of a material that reflects x-radiation and/or strongly absorbs it, the upper run of the endless belt rests on a support face of the belt body, and the belt body, in the vicinity of the x-ray beam, has a notchlike recess, through which the x-ray beam passes.

7. The apparatus of claim 6, wherein the conveyor device is filled, at least in the vicinity of the support face, with a material which transmits the x-radiation essentially completely or with only slight damping.

8. The apparatus of claim 6, wherein at least a portion of the outer wall of the belt body, in the vicinity of the notchlike recess that is unaffected by the recess, acts a part of a wall of a radiation protection housing.

9. The apparatus of claim 6, wherein the belt body includes a substantially U-shaped profile section with two side walls and a top wall forming the support face and connecting the side walls.

10. The apparatus of claim 9, wherein the U-shaped profile section is produced by bending a plate-shaped part, which reflects and/or strongly absorbs x-radiation and which has an aperture that forms the recess for the x-ray beam.

11. The apparatus of claim 10, wherein the U-shaped profile section has two transverse walls of a material that reflects x-radiation and/or strongly absorbs it, and a first transverse wall, viewed in the conveying direction, is provided upstream of the recess, and a second transverse wall is provided downstream of the recess for the x-ray beam, and a bottom wall together with the transverse walls and regions of the top wall that are located respectively upstream and downstream of the recess has a radiation trap for absorbing a substantial quantity of the x-radiation of the fanlike beam that does not pass through the recess on a substantially rectilinear course.

12. The apparatus of claim 3, wherein the belt body, in its support face, has a channel, extending in the conveying direction, which channel extends in a lateral marginal region of the support face, which region, viewed in the conveying direction, is no longer interrupted by the recess, and the channel is engaged by an engagement means of the endless belt.

13. The apparatus of claim 1, wherein the x-radiation source, together with a high-voltage source of the radiation generating device, is positioned in a linearly displaceable fashion via a linear displacement device.

14. The apparatus of claim 1, wherein the radiation generating device is configured as a unit together with the linear displacement device, wherein the unit can be disassembled, as a whole, from the apparatus for x-radiation.

15. The apparatus of claim 1, wherein the x-radiation source is configured and positioned such that the upper marginal beam of the fanlike x-ray beam extends horizontally, and the evaluation and control unit is embodied such that it triggers the linear displacement device in such a way that the upper marginal beam essentially matches a predetermined height position.

16. The apparatus of claim 1, wherein the x-radiation source is configured and positioned such that the fanlike x-ray beam has a horizontally extending partial beam, and the evaluation and control unit is embodied such that it triggers the linear displacement device in such a way that the partial beam essentially matches a predetermined height position.

17. The apparatus of claim 3, wherein the engagement means is a raised area extending in the conveying direction on the underside of the endless belt, in order to absorb displacement forces which act on the upper run of the endless belt in a direction transverse to the conveying direction.

18. The apparatus of claim 7, wherein the material in the vicinity of the recess forms a part of the support face.

19. The apparatus of claim 10, wherein the plate-shaped part is flat.

20. The apparatus of claim 10, wherein the plate-shaped part is a sheet metal part.

* * * * *